United States Patent [19]

Brown et al.

[11] Patent Number: 4,888,169
[45] Date of Patent: Dec. 19, 1989

[54] BORDETELLA BRONCHISEPTICA VACCINE

[75] Inventors: Albert L. Brown; Joseph C. Frantz; Richard H. Peetz, all of Lincoln, Nebr.

[73] Assignee: Norden Laboratories, Inc., Lincoln, Nebr.

[21] Appl. No.: 270,428

[22] Filed: Nov. 9, 1988

Related U.S. Application Data

[63] Continuation of Ser. No. 918,424, Oct. 14, 1986, abandoned.

[51] Int. Cl.$^4$ .................... A61K 39/02; A61K 39/12; A61K 39/38
[52] U.S. Cl. ........................ 424/92; 424/89; 424/93
[58] Field of Search ............... 424/92, 89, 93
[56] References Cited

U.S. PATENT DOCUMENTS

| | | |
|---|---|---|
| 3,845,050 | 10/1974 | Lebkuecher et al. ............ 544/238 |
| 3,873,691 | 3/1975 | Kasuga et al. ............ 424/92 |
| 3,975,388 | 8/1986 | Hakim et al. ............ 544/239 |
| 3,983,229 | 9/1976 | Relyveld ............ 424/89 |
| 4,016,253 | 4/1977 | Switzer et al. ............ 424/92 |
| 4,088,762 | 5/1978 | Hakim et al. ............ 514/252 |
| 4,188,375 | 2/1980 | Straub ............ 424/92 |
| 4,203,970 | 5/1980 | Carlo et al. ............ 424/92 |
| 4,225,583 | 9/1980 | Switzer et al. ............ 424/92 |
| 4,353,905 | 10/1982 | Sircar et al. ............ 514/252 |
| 4,372,945 | 2/1983 | Likhite ............ 424/92 |
| 4,402,939 | 9/1983 | Fournier ............ 424/92 |
| 4,456,588 | 6/1984 | Shimizu ............ 424/92 |
| 4,551,455 | 11/1985 | Hilboll et al. ............ 514/252 |
| 4,705,686 | 11/1987 | Scott et al. ............ 424/92 |

FOREIGN PATENT DOCUMENTS

| | | |
|---|---|---|
| 75436 | 9/1982 | European Pat. Off. . |
| 167995 | 7/1984 | European Pat. Off. . |
| 178875 | 10/1984 | European Pat. Off. . |
| 134868 | 3/1985 | European Pat. Off. ............ 424/92 |
| 142193 | 5/1985 | European Pat. Off. ............ 424/92 |
| 175363 | 6/1985 | European Pat. Off. . |
| 180564 | 5/1986 | European Pat. Off. ............ 424/92 |
| 2436605 | 4/1986 | France ............ 424/92 |

OTHER PUBLICATIONS

Andreescu et al. "Comparative Studies on Pertussis Vaccine Batches Inactivated with Glutanaldehyde, $\beta$-Propiolactone, Formaldehyde or Thiomensal", *Arch Roum Path Exp Microbiol*, T. 38, No. 5, pp. 299-308, Dec., 1979.
Andreescu et al. GA. 93#155762u (1980).
Relyveld GA. 79#135223b (1973).
Peppler et al., *Infect. Immun.*, 44(3): 681 (1984).
Musser et al., *J. Bact.* 166:230 (1986).
Goodnow et al., *Am. J. Vet. Res.* 44:207 (1983).
G. R. Brown et al., J. Chem. Soc. Chem. Commun., 1984, 1373.

*Primary Examiner*—John Kight
*Assistant Examiner*—Nathan M. Nutter
*Attorney, Agent, or Firm*—Edward T. Lentz; Janice E. Williams; Alan D. Lourie

[57] ABSTRACT

A vaccine for protecting canines against infection by *Bordetella bronchiseptica* is prepared by inactivating whole cells with glutaraldehyde.

16 Claims, No Drawings

BORDETELLA BRONCHISEPTICA VACCINE

This is a continuation of application Ser. No. 06/918,424 filed Oct. 14, 1986 and now abandoned.

FIELD OF THE INVENTION

This invention relates to inactivation of pathogenic bacteria and use of such inactivated bacteria in a vaccine.

BACKGROUND INFORMATION

The members of the genus Bordetella, which presently includes *B. pertussis, B. parapertussis* and *B. bronchiseptica*, are small, gram-negative coccobacilli, 0.2 to 0.3 μm by 0.5 to 1.0 μm. They appear singly, in pairs and in small clusters. Their morphology and physiology are more fully described in *Zinsser Microbiology*, 17th edit., edit. by Joklik et al., 1980, Appleton-Century-Crafts, New York, pages 614–624.

Bordetella species are serious pathogens of the respiratory tract in a wide variety of mammals, including man. *B. bronchiseptica* is a primary causative agent of atrophic rhinitis and pneumonia in pigs and of infectious tracheobronchitis ("Kennel Cough") in dogs. *B. pertussis* and, to a lesser extent, *B. parapertussis* and *B. bronchiseptica* cause whooping cough in man.

Peppler et al., *Infect. Immun.* 44(3):681 (1984), describe phenotypic variation of Phase I, II and III *B. bronchiseptica* strains. Similar phenotypic variation occurs in *B. pertussis* and *B. parapertussis*.

Musser et al., *J. Bact.* 166:230 (1986), discuss the interrelatedness of Bordetella species.

Goodnow et al., *Am. J. Vet. Res.* 44:207 (1983), report presence of a heat-labile toxin in *B. bronchiseptica* extracts and suggest a role for such toxin in pathogenesis.

Robinson et al., *Infect. Immun.* 40:523 (1983), report that a protein produced by *B. pertussis* known variously as lymphocytosis-producing factor hemagglutinin (LPF), histamine-sensitizing factor, islet-activating protein, pertussis toxin and pertussigen is important for protection in an intracerebral (i.c.) mouse protection test. Affinity purified LPF was treated with glutaraldehyde to detoxify the protein.

Sekiya et al., *Infect Immun.* 41:598 (1983), report vaccination of mice with formalin-inactivated *B. bronchiseptica*.

Relyveld et al., *C.R. Acad. Sc. Paris*, t277, Serie D, 613–616 (1973), and Relyveld et al., Toxicon 1976, Suppl. 1 (Toxins: Animal, Plant and Microbiol.), pages 1045–1065, disclose preparation of a *B. pertussis* vaccine by glutaraldehyde inactivation.

To date, there has not been a satisfactory vaccine for protecting canine animals against infection by *Bordetella bronchiseptica*. The formalinized or otherwise inactivated whole cell vaccines which have been employed cause undesirable side effects, predominantly including transient lethargy, anorexia and vomiting.

SUMMARY OF THE INVENTION

It has now been found that a safe and effective vaccine for protecting canines from disease caused by *Bordetella bronchiseptica* can be prepared by inactivating whole cells by treatment with glutaraldehyde. Thus, in one aspect, this invention is a vaccine for protecting a canine animal against disease caused by *Bordetella bronchiseptica* comprising a vaccinal amount of whole *Bordetella bronchiseptica* organisms which have been inactivated by treatment with glutaraldehyde.

In a second aspect, the invention is such vaccine which further comprises a vaccinal amount of one or more other antigenic components for protecting a canine animal against disease caused by one or more other pathogenic microorganisms, viruses or cells.

In a further aspect, the invention is a method for protecting a canine animal from disease which comprises internally administering the vaccine of the invention.

DETAILED DESCRIPTION OF THE INVENTION

The vaccine of the invention comprises a vaccinal, i.e., effective and non-toxic, amount of whole *Bordetella bronchiseptica* organisms which have been inactivated by treatment with glutaraldehyde. Typically, the vaccine is prepared by addition of glutaraldehyde to a culture of a non-attenuated strain of *B. bronchiseptica*.

Bordetella organisms for use in preparing a vaccine of this invention are available from a variety of sources including various public and private depositories and clinical infections. Bordetella colonies on Bordet-Gengou agar are known to exist in distinct morphological types. These have been classed into Phase I, II and III. See, Peppler et al., *Infect. Immun.* 44 (3):681 (1984). In this invention, non-attenuated Phase I Bordetella are preferably employed.

For initial growth and propagation, the Bordetella organisms can be cultured on a variety of nutrient media. Bordet-Gengou medium (BG) and synthetic minimal medium, as described by Parker, *Adv Appl. Micro.* 20:27–41(1976), ("Charlotte Parker's minimal medium," i.e., "CPM"), are prefered. Both can be prepared using commercially available media. BG, for example, can be prepared by adding 20% defibrinated sheep blood to basal medium such as is supplied by BBL, Division of Becton Dickinson, Cockeysville, Maryland. Bordetella organisms are cultured at 30° to 45° C., preferably 35°–40° C. and most preferably at 36°–38° C., at approximately neutral pH, e.g., 6.5–7.5, preferably 6.7–7.1. For best growth, liquid cultures are agitated and aerated throughout fermentation. To prepare production cultures, seed cultures are serially propagated in accordance with standard techniques. Production cultures are seeded with at least a 1%, preferably 5 to 10%, inoculum of actively growing cells. Fermentation, prior to inactivation, is typically continued until nutrients are substantially depleted, i.e., depleted or nearly depleted, e.g., 18 to 36 hours. The organisms used in bacterin preparation are passaged for propagation and preferably remain substantially non-attenuated throughout serial passage and production culture.

To prepare the bacterin used in vaccine formulation, glutaraldehyde is added to an active culture having achieved a cell density of at least 3,000 nephelometric units, preferably 4500 to 10,000 nephelometric units. Nephelometric units are determined using a NephoColorimeter which has been calibrated with a standard of certified accuracy, for example, a Coleman Certified Nephelo Standard N=78, and a dilution blank solution, for example, physiological saline. The method used to calibrate the Nephelo-Colorimeter is commonly referred to as the "null method" in which the instrument has been calibrated such that a linear relationship exists for all nephelo values between the dilution blank solution, which is zero, and the certified standard such as the N=78. Samples of unknown nephelometric values are diluted stoichiometrically in dilution blank solution so that when measured in the calibrated instrument, the value of the diluted sample is betweeen zero and 78 nephelometric units. This value is then multiplied by the dilution factor to determine the nephelometric value of the undiluted sample.

Glutaraldehyde is added to a final concentration of 0.15 to 0.25 weight percent (wt. %), preferably 0.20, wt. percent glutaraldehyde per 5000 nephelometric units. The culture is incubated in a presence of glutaraldehyde until complete inactivation has occurred, typically at least 12 hours. An equimolar amount of L-lysine can then be added to complex residual free glutaraldehyde. Finally, a preservative such as thimerosal or other known disinfecting agent suitable for internal administration can be added to the bacterin. Typically, the bacterin will then be diluted to prepare a vaccine formulation containing an effective amount per unit dose. The diluent can be any pharmaceutically acceptable solvent, e.g., physiological saline.

An effective amount of the bacterin is determined by standard techniques as that amount which does not cause unacceptable adverse reactions but which is effective in inducing an immune response in a canine animal such that the host is substantially protected against development of clinical symptoms associated with infection by Bordetella bronchiseptica, i.e., Kennel Cough. An effective amount for protecting canine animals is typically in the range of 250 to 750, preferably about 500, nephelometric units per dose (based on nephelometric determination at time of harvest, prior to inactivation). Such dose typically is administered to a canine animal in a dose volume of 0.5 to 3 ml, preferably about 1 ml in a two dose course, the second dose being 1 to 5, preferably 2–4, weeks after the first. The vaccine is administered internally, e.g., parenterally, preferably by subcutaneous or intramuscular injection such as in the neck region of a dog or other domestic animal. The vaccine is preferably administered to puppies 6 to 12, preferably about 9, weeks old. Intramuscular may be the preferred route of administration in puppies. Annual revaccination with a single dose is recommended for all dogs.

Vaccination with the vaccine of this invention has been shown to be effective in preventing respiratory disease symptoms associated with B. bronchiseptica infection in dogs and, surprisingly, to be free of the undesirable side efects typically associated with known whole cell vaccines. For example, thimerosalinactivated bacterins and attenuated live vaccines for protecting canine animals against Kennel Cough have been associated with transient lethargy, anorexia and vomiting b 1–6 hours following vaccination in up to ⅓ of dogs inoculated. Such effects are typically not observed with the vaccine of the invention. In an extensive field trial in which over 9,000 doses of the B. bronchiseptica vaccine of the invention were administered to dogs, there were only 1 in 400 reports of such side effects (0.23%).

A typical preparation of a vaccine for protecting canines against the clinical symptoms of infection by B. bronchiseptica is as follows.

A master seed stock of non-attenuated B. bronchiseptica is maintained as a lyophilized culture at 2°–7° C. For preparation of working seed, a sample is restored with sterile distilled water and spread onto a Bordet-Gengou plate. Following incubation at 27°±1° C. for 24 to 48 hours, typical smooth colonies (Phase I) are selected for culture in liquid medium.

Seed culture and production cultures are examined microscopically for motility and by gram stain for morphology. Cultures are also confirmed for (+) citrate utilization, (+) nitrate reduction, (−) $H_2S$ production and (+) urea utilization.

Following serial passage for propagation, a seed culture is inoculated into minimal medium in a fermentor and incubated at 37°±1° C. to a cell density of at least 4500 nephelometric units (typically 18–36 hours, often times 20–30 hours) with continuous agitation and aeration.

At harvest, the pH of the culture is adjusted to approximately 6.8 with concentrated HCl and a nephelometric value is determined. Glutaraldehyde is added to yield a final concentration of 0.10 to 0.30 weight percent of glutaraldehyde per 5,000 neohelometric units of cells. The treated culture material is stirred in the fermentor at 15° to 45° C., preferably 35° to 40° C., for about an hour. The material is then transferred aseptically into a glass storage vessel wherein incubation at 15° to 30° C, preferably 20° to 24° C., with gentle stirring is continued for approximately 24 hours after which an equimolar amount of sterile lysine is added. The temperature is then lowered to 2° to 7° C. until assembly into dosage unit forms.

To assemble dosage unit forms, the bacterin is diluted with saline to a final cell density of 250 to 750, preferably 500, nephelometric units per 0.5 to 3, preferably 1 ml and packaged in 1.0 ml units in sterile vials. Thus, based on the calculation at time of harvest, each unit dose contains 250 to 750, preferably about 500, nephelometric units. If desired, the bacterin can be lyophilized for subsequent reconstitution with saline or other parenterally acceptable diluent or excipient in accordance with standard veterinary pharmaceutical techniques.

Included within this invention is a combination vaccine for protecting animals against infection by Bordetella and by one or more other pathogenic microorganisms, cells or viruses. Such other vaccinal agent contains additional antigenic components such as a killed or modified whole cell vaccine or a subunit vaccine which, in any event, is combined with the Bordetella bacterin such that all antigenic components are provided in vaccinal amounts. For example, the B. bronchiseptica bacterin can be combined with, for example, modified live Canine Distemper Virus (ML-CDV), modified live canine Adenovirus Type 2 (ML-CAV2), modified live Canine Parainfluenza Virus (ML-CP1) and a Leptosoira, e.g., canicola and ictohemmoraghiae bacterin. Techniques for preparing such combination vaccines are well known. For example, Jaeger et al., Vet. Bull. 44:2163 (abstract) 1974, report a trivalent vaccine comprising inactivated rabies virus, ML-CDV and inactivated canine viral hepatitis virus (CVH) and a tetravalent vaccine comprising inactivated rabies virus, ML-CDV, inactivated CVH and killed leptospira; Ackermann et al., Vet. Bull 46:1894 (abstract) 1976, report a tetravalent vaccine comprising inactivated rabies virus, ML-CDV, inactivated CVH and killed leptospira; Bijlenga, U.S. Pat. No. 4,351,827, disclose a bivalent vaccine comprising ML rabies virus and ML-CDV. To prepare a combination vaccine of the invention, a vaccinal amount of the Bordetella bacterin of the invention, e.g., 250 to 750 nephelometric units per dose as described above, is contained with one or more of such other vaccine components.

EXAMPLES

The Examples which follow are illustrative and not limiting of the vaccine and method of the invention.

EXAMPLE 1

Materials And Methods

Cultures. *B. bronchiseptica* strain 87 was received from Dr. L. E. Carmichael, Cornell University, Ithaca, New York. The organism was originally isolated by Dr. D. A. Bemis from a dog at the James A. Baker Institute for Animal Health. *B. bronchiseptica* strain BC was isolated from a cat by Mr. Jerry G. Bihr of Norden Laboratories, Lincoln, Nebraska.

Media. Trypticase Soy Agar (DIFCO Laboratories, Detroit, Michigan) supplemented with 100,000 units/liter of U.S.P. Potassium Penicillin-G and 150 mg/liter of "Furaltadone" (Norwich Pharmacal Co.) was used as a selective medium for *B. bronchiseptica*. Bordet-Gengou medium was prepared from basal medium (BBL, Cockeysville, Maryland) supplemented with 20% defibrinated sheep's blood. The medium used for vaccine production was the synthetic minimal medium described by Parker, *Adv. Appl. Micro.* 20:27(1976).

The medium is preferrred by (i) dissolving, in order, L-proline (2.40 g), L-glutamic acid (0.67 g), NaCl (2.50 g), $KH_2PO_4$ (0.50 g), KCl (0.20 g), Mg $Cl_2 \cdot 6H_2O$ (0.10 g), $CaCl_2 \cdot 2H_2O$ (0.0265 g) and Trizma base (6.075 g) (Sigma Chemicals, St. Louis, Missouri) in 900 ml of water, (ii) adjusting the pH to about pH 7.2 with HCl, (iii) adding water to a total of 970 ml, (iv) sterilizing the medium by autoclaving and (v) adding to the medium filter-sterilized aliquots (10 ml) of A:L-cystine (0.04 g), B:$FeSO_4 \cdot 7H_2O$ (0.01 g) and C:Ascorbic acid (0.02 g), nicotinamide (0.004 g) and sodium acetate (0.2 g), thereby bringing the total volume from 970 ml to 1 L.

Agglutination Test

Preparation of Antigen: *B. bronchiseptica* strain 87 was grown in 750 ml of synthetic medium at 37° C. with vigorous shaking. Following incubation for about 22 hr., 0.8 ml of formalin was added. After standing for 24 hours at 37° C. the cells were harvested by centrifugation at 10,000×g for 30 min at 5° C. The cells were resuspended to approximately 200 ml in saline containing 0.037 percent formaldehyde. The concentrate was stored under refrigeration. For use, it was diluted 1/20 in Dulbecco's saline solution prepared by dissolving NaCl (6.4 g), $CaCl_2$(0.01 g), and $MgCl_2$ $6H_2O$ (0.01 g) in water to a total volume of 100 ml (q.s.).

Test Procedure: The test was performed in conical bottomed 96 well plastic trays. Dilutions of serum were made in Dulbecco's saline supplemented with 0.01% bovine serum albumin in a volume of 0.05 ml. Sera to be tested were added in a volume of 0.05 ml to the first well and dilutions are made manually. To each well, 0.5 ml of antigen was added. The first well was then considered to be a 1:4 dilution of serum. Standard controls with known positive and negative sera were included within each series. The plates were shaken mechanically for 2 minutes, incubated at 37° for 2 hr. and then overnight at 4° C. The test was read using a stand with a magnifying mirror. A reference to this procedure may be found in a publication by D. L. Harris and W. P. Switzer entitled, "Immunization of Pigs Against *Bordetella bronchiseptica* Infection by Parenteral Vaccination," published in the *Am. J. Veterin. Res.* 33:1975–1984.

Aerosol Exposure of Dogs

Dogs were sedated prior to treatment by inoculation of 44 mg of xylazine ("Rompum," Chemago Division of Bay Chemical Corp., Kansas City, Missouri) per kilogram of body weight. The challenge dose was administered with a model 40 DeVilbiss glass nebulizer (DeVilbiss Company, Medical Products Division, Somerset, Pennsylvania) which was inserted through a hole in the bottom of a styrofoam cup fitted over the dog's muzzle. The culture concentrate was administered from four to eight minutes using 0.7 $Kg/cm^2$ (10 lbs/sq. inch) of air pressure. In a single experiment, the same time period of administration was used for each dog.

The culture for challenge was prepared by reconstituting a vial of lyophilized challenge culture (*B. bronchiseptica* Strain BC) into a flask of Trypticase Soy Broth or Charlotte Parker's Medium. After incubation at 37° C. for approximately 24 hours, a drop of broth culture was transferred to plates of Bordet-Gengou Medium. After an additional 24 hours incubation, the growth was removed and resuspended in saline. It has been found that cultures standardized by nephelometry to $1 \times 10^7$ organisms/ml consistently produced coughing in susceptible dogs.

Selection of Dogs

All dogs used for these studies were screened for antibodies against *B. bronchiseptica* and cultured to verify they were not colonized, and therefore susceptible to infection. Antibodies were detected by the agglutination test. Dogs having serum titers of 1:16 or higher were excluded from the test. Cultures were collected from deep tracheal swabs and plated on selective medium. If a dog was infected, a pure culture of *B. bronchiseptica* was usually obtained. Isolates which were not Bordetella were tentatively identified by a gram stain. Dogs were segregated by litters in isolation rooms. Additional swabs were taken prior to challenge and two weeks following challenge. All cultures taken prior to challenge had to be negative for *B. bronchiseptica* before approving the dog for experimental use.

Collection of Tracheal Swabs

For the routine examination of dogs, it was found that deep tracheal swabs were preferable to nasal swabs. If infected, tracheal swabs were usually pure cultures of *B. bronchiseptica*. Dogs were anesthetized with "Suritol" (Park Davis, Detroit, Michigan) using about 0.1 ml per pound of body weight. While the mouth was held open, a sterile swab was inserted deep into the trachea. The swab was transported in a screw cap tube with 0.1 ml saline. For culturing, the swab was streaked onto the Selective Medium. Cultures were incubated at 37° C. and examined at 48 hours. Growth on selective medium was subcultured to differential media for biochemical identification of *B. bronchiseptica*.

Seed. A working seed has been prepared from the master seed by five passages on Bordet-Gengou blood plates, overnight growth in synthetic medium, and lyophilized. The working seed was checked and found satisfactory.

Bacterin Preparation

Growth of Organisms. Each experimental lot of bacterin was derived from a freshly reconstituted vial of working seed. A drop of reconstituted seed was placed onto Bordet-Gengou blood agar and the plate was struck with a sterile loop to obtain isolated colonies. After 48 hours incubation at 37° C., 10 to 20 typical small, smooth colonies were picked, transferred to 5 to 10 ml of sterile synthetic medium which was immediately transferred to 50 ml of synthetic medium in a 300 ml flask. This starter culture, and the subsequent step-up cultures, were incubated for 18 to 24 hours at 37° C. with vigorous shaking. Step-up growth to 10 liter production fermentors occurred in 500 ml of synthetic medium in a 2 liter flask. Once the 10 liter fermentor was seeded, the culture was incubated at 37° C. for 8 to 24 hours; that is, until the organism no longer demanded oxygen. Dissolved oxygen content was monitored and controlled by aeration with sterile air. The culture was stirred continuously during the growth period. Sterile antifoam solution was used to control foam.

Inactivation. At the time of inactivation, the culture density was determined by nephelometry. The pH of the culture was adjusted to approximately 6.8 and sufficient glutaraldehyde was added to give a ratio of glutaraldehyde to cell density of 0.20 weight percent glutaraldehyde to 5000 nephelometric units of cells. To ensure free aldehyde groups no longer remained, an equimolecular amount of sterile lysine was subsequently added.

Assembly. Four small lots of bacterin were prepared and were assembled according to the proportions shown in Table 1 such that one dose contained 500 nephelometric units of inactivated B. bronchiseptica per ml. Sterile 10% thimerosal was added to a concentration not exceeding 0.01% (W/V).

TABLE 1

Assembly of Experimental Lots of B. bronchiseptica Bacterin

| Component Ferm. Run No. | Experimental Lot | | | |
|---|---|---|---|---|
| | 10 | 11 | 12 | 13 |
| NEPHELOMETRIC VALUE | 6000 | 5000 | 5000 | 7200 |
| Vol. of Culture (ml) | 20.8 | 25 | 25 | 28 |
| Vol. of Sterile Saline (ml) | 229.2 | 225 | 225 | 372 |
| Vol. of Sterile 10% Thimerosal (ml) | 0.025 | 0.025 | 0.025 | 0.4 |

Vaccination and Challenge. Litters of mongrel pups ranging in age from 8 to 20 weeks were purchased locally and brought into our isolation units where they were held as litters throughout the entire test period. Prior to use, all pups were screened for antibodies against B. bronchiseptica and checked twice by tracheal culture for absence of this organism. Pups were kept by litters and, in so far as practical, controls and vaccinates for each serial were selected sequentially.

Two experiments were conducted. The first experiment tested experimental lots 10, 11, and 12; the second tested experimental lots 11, 12, and 13. Pups were vaccinated intramuscularly two times at a two week interval with 1.0 ml dose. Nonvaccinated control dogs received a sham vaccination of saline. Twelve to 28 days following the second vaccination the pups were challenged by aerosol. The pups on the first test were vaccinated in two groups; the first group, Days 0 and 14, and the second, Days 14 and 28. All pups were challenged on Day 42. The pups on the second test were vaccinated on Days 0 and 14 and challenged on Day 30.

Other Tests. The experimental lots were tested for purity, safety, and viricidal activity in accordance with 9 CFR 113.26, 113.38, and 113 35, respectively.

RESULTS

Purity, Safety, and Viricidal Activity. Purity, safety, and viricidal activity tests were performed by the quality assurance division of Norden Laboratories. The results were satisfactory for all tests performed.

Untoward Reactions. All dogs were observed continuously for four hours immediately following vaccination for indications of lethargy, malaise, and seizures of vomiting, and daily thereafter. All dogs remained normal throughout the observation period.

Serology. Serum samples taken prior to vaccination, two weeks later at the second vaccination, prior to challenge, and two weeks post challenge were evaluated for antibody levels by agglutination. Serum from vaccinated dogs showed increased antibody levels prior to challenge, whereas, serum from sham (saline) vaccinated controls dogs did not. Titers from all dogs increased following challenge. The results are summarized in Tables 2 and 3.

TABLE 2

Results of Serum Agglutination Tests

| | | Reciprocal Titers | | | |
|---|---|---|---|---|---|
| Experimental Lot | Dog No. | Pre-Vac | Pre 2nd Vac | Pre Challenge | 2 Weeks Post Challenge |
| 10 | DB38 | 4 | 4 | 512 | 8192 |
| | DB39 | 4 | 4 | 512 | 8192 |
| | DB41 | 4 | 4 | 512 | 8192 |
| | DB42 | <4 | 8 | 1024 | 8192 |
| | A1 | <4 | 8 | 128 | 4096 |
| | A3 | <4 | 4 | 32 | 2048 |
| | A5 | <4 | 8 | 64 | 2048 |
| 11 | D75 | 4 | 64 | 4096 | 8192 |
| | A12 | 8 | 32 | 4096 | 8192 |
| | A15 | 4 | 32 | 2048 | 8192 |
| | A18 | 4 | 4 | 128 | 4096 |
| 12 | D76 | 4 | 4 | 1024 | 4096 |
| | A13 | 4 | 32 | 4096 | 8192 |
| | A16 | 8 | 16 | 256 | 512 |
| | A19 | 4 | 4 | 512 | 8192 |
| Sham (Saline) Vaccinated Controls for Lot 10 | DB40 | <4 | <4 | <4 | 128 |
| | A2 | 4 | 4 | 4 | 64 |
| | A4 | 4 | 4 | 4 | 32 |
| | D74 | 4 | 4 | <4 | 256 |
| | A14 | ≦4 | ≦4 | ≦4 | 256 |
| | A17 | 8 | 4 | 4 | 512 |

TABLE 3

Results of Serum Agglutination Tests

| | | Reciprocal Titers | | | |
|---|---|---|---|---|---|
| Experimental Lot | Dog No. | Pre-Vac | Pre 2nd Vac. | Pre Challenge | 2 Weeks Post Challenge |
| 11 | A26 | 4 | 8 | 1024 | >8192 |
| | A30 | 4 | 16 | 1024 | >8192 |
| | A35 | <4 | 8 | 2048 | 8192 |
| | A39 | 4 | 64 | 4092 | ≧8192 |
| | A43 | 4 | 32 | 2048 | >8192 |
| | A47 | 4 | 16 | 2048 | 4096 |
| | A50 | 4 | 16 | 2048 | 4096 |
| | A54 | 4 | 16 | 2048 | 4096 |
| 12 | A27 | <4 | 8 | 1024 | >8192 |
| | A31 | 4 | 8 | 512 | >8192 |
| | A36 | 4 | 16 | 2048 | 8192 |
| | A40 | 4 | 16 | 128 | 4096 |
| | A44 | 4 | 16 | 4096 | >8192 |
| | A48 | 4 | 16 | 2048 | 8192 |

TABLE 3-continued

Results of Serum Agglutination Tests
Reciprocal Titers

| Experimental Lot | Dog No. | Pre-Vac | Pre 2nd Vac. | Pre Challenge | 2 Weeks Post Challenge |
|---|---|---|---|---|---|
| | A51 | 4 | 32 | 4096 | >8192 |
| | A55 | 4 | 16 | 512 | 4096 |
| 13 | A28 | 4 | 32 | 2048 | >8192 |
| | A32 | 4 | 16 | 512 | 4096 |
| | A37 | 4 | 16 | 1024 | 2048 |
| | A41 | 4 | 64 | 2048 | >8192 |
| | A45 | 4 | 4 | 128 | 4096 |
| | A49 | 4 | 16 | 2048 | 4096 |
| | A52 | 4 | 8 | 128 | 4096 |
| | A56 | 4 | 16 | 2048 | 8192 |
| Sham (Saline) | A25 | 4 | 4 | 4 | 32 |
| Vaccinated | A29 | 4 | 4 | 4 | 128 |
| Controls for | A33 | 4 | 4 | 4 | 256 |
| Lots 11, 12, | A34 | <4 | <4 | <4 | 512 |
| & 13 | A38 | 4 | 4 | 4 | 128 |
| | A42 | <4 | 4 | <4 | 128 |
| | A46 | 4 | 4 | 4 | 2048 |
| | A53 | 4 | 4 | 4 | 256 |

Challenge. Following challenge, pups were observed twice each day for 14 consecutive days for clinical signs of disease. Failure to protect was defined as coughing or other indication of clinical disease on two consecutive days. Artificial stimulation to produce the coughing reflex was not used. The results are presented in Tables 4 and 5 and summarized in Table 6.

TABLE 4

Daily Observations on Dogs in Experiment 1 Following Aerosol Challenge

| Experimental Lot | Dog No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 10 | DB38 | N | N | N | N | N | N | N | N | N | N | N | N | N | N |
| | DB39 | N | N | N | N | N | N | N | N | N | N | N | N | N | N |
| | DB41 | N | N | N | N | N | N | N | N | N | N | N | N | N | N |
| | DB42 | N | N | N | N | N | N | N | N | N | N | N | N | N | N |
| | A1 | N | N | N | N | N | N | N | N | N | N | N | N | N | N |
| | A3 | N | N | N | N | C | C | C | N | N | N | N | N | N | N |
| | A5 | N | N | N | C* | C | C | C | N | N | N | N | N | N | N |
| 11 | D75 | N | N | N | N | C* | N | C | N | C* | N | N | N | N | N |
| | A12 | N | N | N | N | N | N | N | N | N | N | N | N | N | N |
| | A15 | N | N | N | N | C* | C* | C | N | N | N | N | N | N | N |
| | A18 | N | N | N | N | N | N | N | N | N | N | N | N | N | N |
| 12 | D76 | N | N | N | N | C | N | N | N | N | N | N | N | N | N |
| | A13 | N | N | N | N | N | N | N | N | N | N | N | N | N | N |
| | A16 | N | N | N | N | N | C* | N | N | N | C* | N | N | N | N |
| | A19 | N | N | N | N | N | C* | N | N | N | N | N | N | N | N |
| Controls | DB40 | N | N | N | C | C | C | C | C | C* | N | N | N | N | N |
| | A2 | N | N | N | N | C* | C | C | N | C* | C* | N | N | N | N |
| | A4 | N | N | N | N | N | C | C | N | C* | C* | N | N | N | N |
| | D74 | N | N | N | N | N | C | C | N | N | N | N | N | N | N |
| | A14 | N | N | N | N | C | C | C | N | N | N | N | N | N | N |
| | A17 | N | N | N | N | N | N | N | N | N | N | N | N | N | N |

+N dog was normal during period of observation.
C dog was observed coughing during both observation periods this day.
C* dog was observed coughing during one observation period this day.

TABLE 5

Daily Observations on Dogs in Experiment 2 Following Aerosol Challenge

| Experimental Lot | Dog No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 11 | A26 | N | N | N | N | N | N | N | N | N | N | N | N | N | N |
| | A30 | N | N | N | N | C* | C* | N | N | N | N | N | N | N | N |
| | A35 | N | N | N | N | N | N | N | N | N | N | N | N | N | N |
| | A39 | N | N | N | N | N | N | N | N | N | N | N | N | N | N |
| | A43 | N | N | N | N | N | N | N | N | N | N | N | N | N | N |
| | A47 | N | N | N | N | N | N | N | N | N | N | N | N | N | N |
| | A50 | N | N | N | N | N | C* | N | N | N | N | N | N | N | N |
| | A54 | N | N | N | N | N | N | N | N | N | N | N | N | N | N |
| 12 | A27 | N | N | N | N | C | C | C | C | C | C* | C* | C | N | N |
| | A31 | N | N | N | N | N | C* | C* | N | N | N | N | N | N | N |
| | A36 | N | N | N | N | N | N | N | N | N | N | N | N | N | N |
| | A40 | N | N | N | N | N | N | N | N | N | N | N | N | N | N |
| | A44 | N | N | N | N | N | N | N | N | N | N | N | N | N | N |
| | A48 | N | N | N | N | C* | N | N | N | N | N | N | N | N | N |
| | A51 | N | N | N | N | N | N | N | N | N | N | N | N | N | N |
| | A55 | N | N | N | N | N | N | N | N | N | N | N | N | N | N |
| 13 | A28 | N | N | N | N | N | N | N | N | N | N | N | N | N | N |
| | A32 | N | N | N | N | N | N | N | N | C | C* | N | N | N | N |
| | A37 | N | N | N | N | N | N | N | N | N | N | N | N | N | N |
| | A41 | N | N | N | C* | N | N | N | N | N | N | N | N | N | N |
| | A45 | N | N | N | N | N | C* | N | N | N | N | N | N | N | N |
| | A49 | N | N | N | N | N | C* | N | N | N | N | N | N | N | N |
| | A52 | N | N | N | N | N | N | N | N | N | N | N | N | N | N |
| | A56 | N | N | N | N | N | N | N | N | N | N | N | N | N | N |

TABLE 5-continued

Daily Observations on Dogs in Experiment 2 Following Aerosol Challenge

| Experimental Lot | Dog No. | Daily Observations+ | | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Sham (Saline) | A25 | N | N | N | N | C* | C | C* | C | C* | C* | C* | C* | N | N |
| Vaccinated | A29 | N | N | N | N | C | C | C | C | C | C* | C* | N | C | N |
| Controls For | A33 | N | N | N | N | C* | C | N | C* | N | C | C | N | N | N |
| Lots 11, 12, | A34 | N | N | N | N | C | C | C | C | C* | C* | N | N | N | N |
| & 13 | A38 | N | N | N | N | C* | C | C* | N | N | N | N | N | N | N |
| | A42 | N | N | N | N | C | C* | N | N | N | N | N | N | N | N |
| | A46 | N | N | N | N | N | C | C* | N | N | N | N | N | N | N |
| | A53 | N | N | N | N | C | C | C | C | C* | N | C* | N | N | N |

TABLE 6

Summary of Results Experiments 1 and 2 (Aerosol Challenge).

| Experiment | Lot No. | Clinical Signs (coughing) | Remained Normal |
|---|---|---|---|
| 1 | 10 | 2 | 5 |
| | 11 | 1 | 3 |
| | 12 | 0 | 4 |
| | Control | 5 | 1 |
| 2 | 11 | 1 | 7 |
| | 12 | 2 | 6 |
| | 13 | 1 | 7 |
| | Control | 8 | 0 |
| Combined | 10 | 2 | 5 |
| | 11 | 2 | 10 |
| | 12 | 2 | 10 |
| | 13 | 1 | 7 |
| | Control | 13 | 1 |

Throat swabs collected from selected pups (vaccinates and controls) two weeks post challenge uniformly showed colonization with *B. bronchiseptica*.

Analysis of results by the Chi-Square Test shows that all four experimental lots are satisfactory at P<5%. Lot 10 was satisfactory in experiment 1. Lots 11 and 12 were inconclusive because of the number of dogs in the test. In experiment 2, lots 11, 12, and 13 were satisfactory. The combined results from both experiments also showed lots 11 and 12 to be satisfactory.

The canine potency test used to evaluate this product is reliable because it closely approximates the disease naturally observed in the host animal and depends upon a natural route of infection for exposure. The difficulty with it is in obtaining dogs without prior exposure. Our criteria for dogs were strict. Dogs must have been serologically negative and free from *B. bronchiseptica* as determined by two tracheal swabs taken two weeks apart so that dogs are in isolation for at least two weeks before the second specimen is collected.

One problem with the Bordetella bacterins, heretofore, has been that they produced an unacceptable toxic reaction in too great a percentage of pups shortly after administration. Within the next few hours after leaving the veterinary clinic, a vaccinated dog's owner might observe lethargy, malaise, or seizures of vomiting. Despite the fact that the product provided protection, veterinarians were reluctant to use this product.

An adjuvant was not used in preparing these bacterins because good potency was obtained without one. However, aluminum hydroxide as well as other parenterally-tolerated adjuvants can be employed in the vaccine of the invention.

EXAMPLE 2

Materials And Methods

Canine Parainfluenza Vaccine. Canine parainfluenza virus strain NL-CPI-5, a strain licensed by the United States Department of Agriculture, was cultured and harvested in Norden Laboratories production facility. A small experimental serial was prepared by serially passaging the virus in a canine kidney cell line. The virus was harvested, combined with a stabilizer (40% by volume) and lyophilized in one ml dosage units. Each dosage unit contained $10^{7.3}$ TCID$_{50}$ of modified live virus.

Bordetella bronchiseptica Bacterin. A Pilot Serial of a *Bordetella bronchiseptica* Bacterin was prepared substantially as described in Example 1, above.

Selection of Dogs. All dogs used for this study were screened for antibodies against *B. bronchiseptica* and canine parainfluenza virus. Further, a throat swab was taken from each dog substantially as described above to verify that they were not colanized with *B. bronchiseptica*. Dogs colonized with *B. bronchiseptica* or having serum titers of 1:16 or higher were excluded from the test. Dogs having titers to canine parainfluenza of 1:4 or greater were likewise excluded.

Vaccination. The *Bordetella bronchiseptica* bacterin was used to aseptically rehydrate the Canine Parainfluenza Vaccine. Vaccinations were administered intramuscularly as a 1.0 ml dose on 2 occasions with a 14 day interval. Dogs were closely observed for 3 to 4 hours following each administration of vaccine for development of untoward reactions.

Serological Evaluation. Sera were collected prior to the initial, and two weeks following the final, vaccinations. Antibody levels to *B. bronchiseptica* were determined by an agglutination test. Antibody levels to canine parainfluenza virus were performed using standard methods.

RESULTS

Untoward Reactions. All dogs were observed continuously for 3 to 4 hours immediately following vaccination for indications of lethargY, malaise, and seizures of vomiting, and dailY thereafter. All dogs remained normal throughout the observation period.

Serology. Results of serological evaluation of pre- and post-vaccination sera are shown in Table 1—2. Prior to vaccination, the sera of all dogs were essentially negative for antibodies to both components. The serum antibody levels for all dogs increased following the vaccination regimen and were consistent with titers of dogs which have been shown to be protected from challenge with virulent strains of either pathogen.

TABLE 1-2

Serological evaluation of dogs vaccinated with Canine Parainfluenza Vaccine, Modified Live Virus, in combination with Bordetella Bronchiseptica Bacterin.

| COMPONENT ADMINISTRATED | DOG NO. | SEROLOGICAL TITRATION | | | |
|---|---|---|---|---|---|
| | | B. BRONCHISEPTICA | | PARAINFLUENZA | |
| | | PRE | POST | PRE | POST |
| Canine Parainfluenza Vaccine | B-40 | Neg | 256 | Neg | 512 |
| Bordetella Bronchiseptica Bacterin | B-41 | Neg | 1024 | 2 | ≧512 |
| | B-42 | Neg | 1024 | 2 | ≧512 |
| | B-43 | Neg | 32 | Neg | ≧512 |
| | B-44 | 4 | 2048 | 2 | ≧512 |
| | B-45 | Neg | 256 | 2 | ≧512 |
| | B-46 | Neg | 32 | 2 | 256 |
| | B-47 | Neg | 1024 | 2 | 256 |
| | B-48 | 4 | 8192 | Neg | 256 |
| | Geometric Mean | 4.7 | 474 | 1.6 | 406 |

Results of serological evaluation of the Pilot Serial of Bordetella Bronchiseptica Bacterin are presented in Table 2—2. We evaluated an increase in serum antibody level, as measured by agglutination, to reflect exposure to B. bronchiseptica surface antigens, either through vaccination or by natural infection. Although the agglutination titer may not be a direct measurement of antibody levels to protective antigens, it is the strongest indicator of a post vaccination response at our disposal and, historically, has been consistent with protection in challenge of immunity studies. Some dogs demonstrate indications of disease regardless of their serum agglutination titer. Conversely, other data show protection in dogs having a titer of as low as 4 at the time of challenge. We evaluated the agglutination titer for B. bronchiseptica herein to be satisfactory when compared to antibody levels observed in dogs, at the time of challenge, which were protected.

TABLE 2-2

Serological evaluation of dogs vaccinated with Bordetella Bronchiseptica Bacterin

| | DOG NO. | SEROLOGICAL TITRATION | |
|---|---|---|---|
| | | PRE | POST |
| VACCINATED | A59 | NEG | 4096 |
| | A60 | NEG | 1024 |
| | A63 | NEG | 1024 |
| | A64 | NEG | 4096 |
| | A65 | NEG | 2048 |
| | A66 | NEG | 4096 |
| | Geometric Mean | NEG | 2299 |
| NON-VACCINATED CONTROLS | 205 | NEG | NEG |
| | 206 | NEG | NEG |
| | 207 | NEG | NEG |
| | 208 | NEG | NEG |
| | 209 | NEG | NEG |
| | 210 | NEG | NEG |
| | Geometric Mean | NEG | NEG |

The purpose of the combination vaccine described herein is to elicit a protective level of immunity to virulent strains of canine parainfluenza virus and B. bronchiseptica. The data presented herein demonstrate that neither fraction interfered with the immunological response of the other. Further, the levels of serum antibody to both canine parainfluenza virus and B. bronchiseptica were consistent with the levels in animals found to be protected from clinical disease following rigorous challenge.

In a similar study, a combination bacterin containing the gluturaldehyde-inactivated B. bronchiseptica fraction of the invention and inactivated Leptospira canicola and Leotospira icterhemmorhagiae was used to restore dessicated ML-CDV, ML-CAV2, ML-CPI and ML-CPV as contained in VANGUARD ® Canine Distemper-Adenovirus Type 2 - Parainfluenza-Parvovirus Vaccine (Norden Laboratories, Lincoln, Nebraska, U.S.A.). This seven component combination vaccine was administered in 1 ml doses, subcutaneously or intramuscularly to dogs. All dogs developed an immune response indicative of protection to all fractions following a single vaccination except that a booster dose, e.g., 5 to 17 days later, was required to stimulate the desired response to the B. bronchiseptica fraction.

The above description and examples fully disclose this invention and the preferred embodiments thereof. The invention, however, is not limited to the precise constructions herein described but, rather, encompasses all modifications and improvements coming within the scope of the claims which follow.

We claim:

1. A vaccine for protecting a canine animal against disease caused by Bordetella bronchiseptica which comprises a vaccinal amount of whole Bordetella bronchiseptica cells which have been inactivated by treatment with glutaraldehyde.

2. The vaccine of claim 1 which comprises a glutaraldehyde inactivated culture of B. bronchiseptica grown in liquid medium at 35° to 40° C. with aeration for 18–36 hrs. until nutrients are substantially depleted.

3. The vaccine of claim 1 which comprises 250 to 750 nephelometric units, prior to inactivation, within each vaccine dose.

4. The vaccine of claims 1, 2 or 3 which further comprises L-lysine in an amount required to complex residual free glutaraldehyde groups.

5. The vaccine of claims 1, 2 or 3 which comprises 500 nephelometric units, prior to inactivation, per ml.

6. The vaccine of claim 5 which further comprises an amount of L-lysine equimolar to the amount of glutaraldehyde and 0.001 to 0.01% thimerosal.

7. The vaccine of claim 1 which further comprises a vaccinal amount of one or more additional antigenic components for protecting a canine animal against disease caused by one or more other pathogenic microorganisms, cells or viruses.

8. The vaccine of claim 7 in which the additional antigenic components are one or more of inactivated Leptospira canicola, inactivated Leptospira icterhemmorhagiae, modified canine distemper virus, modified canine adenovirus type 2, modified canine parainfluenza virus and modified canine parvovirus.

9. A method for protecting a canine an against disease caused by *Bordetella bronchiseptica* which comprises internally administering to the animal a vaccine comprising a vaccinal amount of whole *Bordetella bronchiseptica* cells which have been inactivated by treatment with glutaraldehyde.

10. The method of claim 9 in which the vaccine comprises a glutaraldehyde inactivated culture of *B. bronchiseptica* grown in liquid medium at 35° to 40° C. for 18–36 hrs. with aeration until nutrients are substantially depleted.

11. The method of claim 9 in which the vaccine comprises 250 to 750 nephelometric units, prior to inactivation, within each vaccine dose.

12. The method of claims 9, 10 or 11 in which the vaccine further comprises L-lysine in an amount required to complex residual free aldehyde groups.

13. The method of claims 9, 10 or 11 which the vaccine comprises 500 nephelometric units, prior to inactivation, per ml.

14. The method of claim 13 in which the vaccine further comprises an amount of L-lysine equimolar to the amount of glutaraldehyde and 0.001 to 0.01% thimerosal.

15. The method of claim 9 in which the vaccine further comprises a vaccinal amount of one or more additional antigenic components for protecting a canine animal against disease caused by one or more other pathogenic microorganisms, cells or viruses.

16. The method of claim 15 in which the additional antigenic components are one or more of inactivated *Leptospira canicola* inactivated, *Leptospira icterhemmorhagiae*, modified canine distemper virus, modified canine adenovirus type 2, modified canine parainfluenza virus and modified canine parvovirus.

* * * * *